United States Patent
Soni et al.

(10) Patent No.: US 7,619,095 B2
(45) Date of Patent: Nov. 17, 2009

(54) PROCESS FOR THE PREPARATION OF INDOLONE DERIVATIVE

(75) Inventors: Rohit Ravikant Soni, Vadodara (IN); Hitarth Harshendu Acharya, Vadodara (IN); Hetal Rameshchandra Shah, Vadodara (IN); Trushar Rajnikant Shah, Vadodara (IN); Buchi Reguri Reddy, Vadodara (IN)

(73) Assignee: Alembic Limited, Gujarat (IN)

( * ) Notice: Subject to any disclaimer, the term of this patent is extended or adjusted under 35 U.S.C. 154(b) by 76 days.

(21) Appl. No.: 11/816,343

(22) PCT Filed: Feb. 15, 2006

(86) PCT No.: PCT/IN2006/000052

§ 371 (c)(1),
(2), (4) Date: Aug. 15, 2007

(87) PCT Pub. No.: WO2006/123356

PCT Pub. Date: Nov. 23, 2006

(65) Prior Publication Data

US 2008/0262244 A1    Oct. 23, 2008

(30) Foreign Application Priority Data

Feb. 15, 2005    (IN) .......................... 77/MUM/2005

(51) Int. Cl.
C07D 209/14    (2006.01)
A61K 31/4045    (2006.01)
(52) U.S. Cl. ...................................... 548/469; 514/415
(58) Field of Classification Search ................. 548/469; 514/415
See application file for complete search history.

(56) References Cited

U.S. PATENT DOCUMENTS 4,452,880 A    6/1984    Seino et al.

FOREIGN PATENT DOCUMENTS

CN    200510027164.4    *    6/2005

OTHER PUBLICATIONS

Accession No. 2007:14385 Caplus abstract of CN Application 200510027164.4, to Pan et al.*
Gallagher et al., "4[2-(Di-n-propylamino)ethyl]-2(3H)indolone: A prejunctional dopamine receptor agonist." J. Med. Chem 28(1985): 1533-1536.*
Sorkin et al., "Beitrage zum Problem der Ahnlichkeit in der CHemie II." Helv. Chim. Acta (1948): 65-75. XP002401416.
Gallagher et al., "4-[2-(Di-n-propylamino)ethyl]-2(3H)indolone: A prejunctional dopamine receptor agonist." J. Med. Chem 28(1985): 1533-1536. XP002401417.
International Search Report for PCT/IN2006/000052.

* cited by examiner

Primary Examiner—Joseph K. McKane
Assistant Examiner—Janet L Coppins
(74) Attorney, Agent, or Firm—Merchant & Gould P.C.

(57) ABSTRACT

A process for the preparation of 4-[2-(Di-n-propylamino) ethyl]-2,3-dihydro-1H-indol-2-one of formula (I) and its pharmaceutically acceptable salts, solvates Formula I involving new intermediates of compound of formula (A) and (B) wherein R represents (i) a halogen atom selected from fluorine, chlorine atom, bromine atom and iodine atom; (ii) lower alkanesulfonyloxy group selected from methanesulfonyloxy, ethanesulfonyloxy, isopropanesulfonyloxy, propanesulfonyloxy, butanesulfonyloxy, tert-butanesulfonyloxy, pentanesulfonyloxy, hexanesulfonyloxy; (iii) substituted or unsubstantiated arylsulfonyloxy group selected from phenylsulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy; (iv) arylalkylsulfonyloxy group selected from benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy.

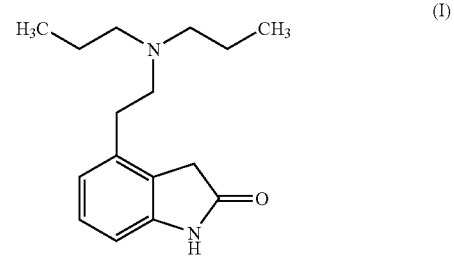

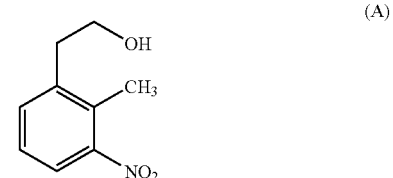

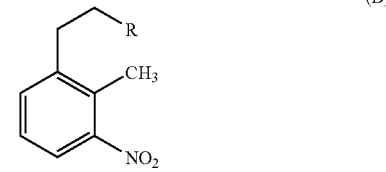

25 Claims, No Drawings

PROCESS FOR THE PREPARATION OF INDOLONE DERIVATIVE

FIELD OF THE INVENTION

The present invention relates to the process for the preparation of 4-[2-(Di-n-propylamino)ethyl]-2,3-dihydro-1H-indol-2-one of formula (I) and its pharmaceutically acceptable salts. Also, the present invention relates to the novel compounds, which can be used as intermediate in the preparation of compound of formula (I). The compound of formula (I) is commonly known as Ropinirole, which is useful in the treatment of Parkinson's disease. Moreover, the present invention is pertaining to novel process for the preparation of Ropinirole hydrochloride.

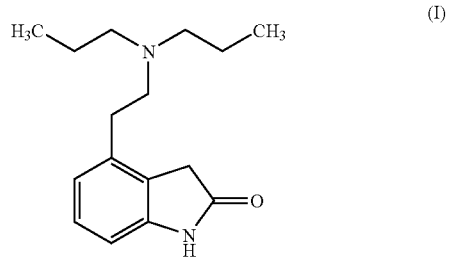

BACKGROUND AND PRIOR ART

Ropinirole is a dopamine agonist and having selective affinity for dopamine D2-like receptors and little or no affinity for non-dopaminergic brain receptors. Ropinirole is indicated as adjunct therapy to levodopa in patients with advanced Parkinson's disease. Also, recent clinical trials have focused on its use, as monotherapy in patients with early Parkinson's disease Ropinirole was first reported in U.S. Pat. No. 4,452,880. It discloses the process for the preparation of Ropinirole hydrochloride as shown in following Scheme-1

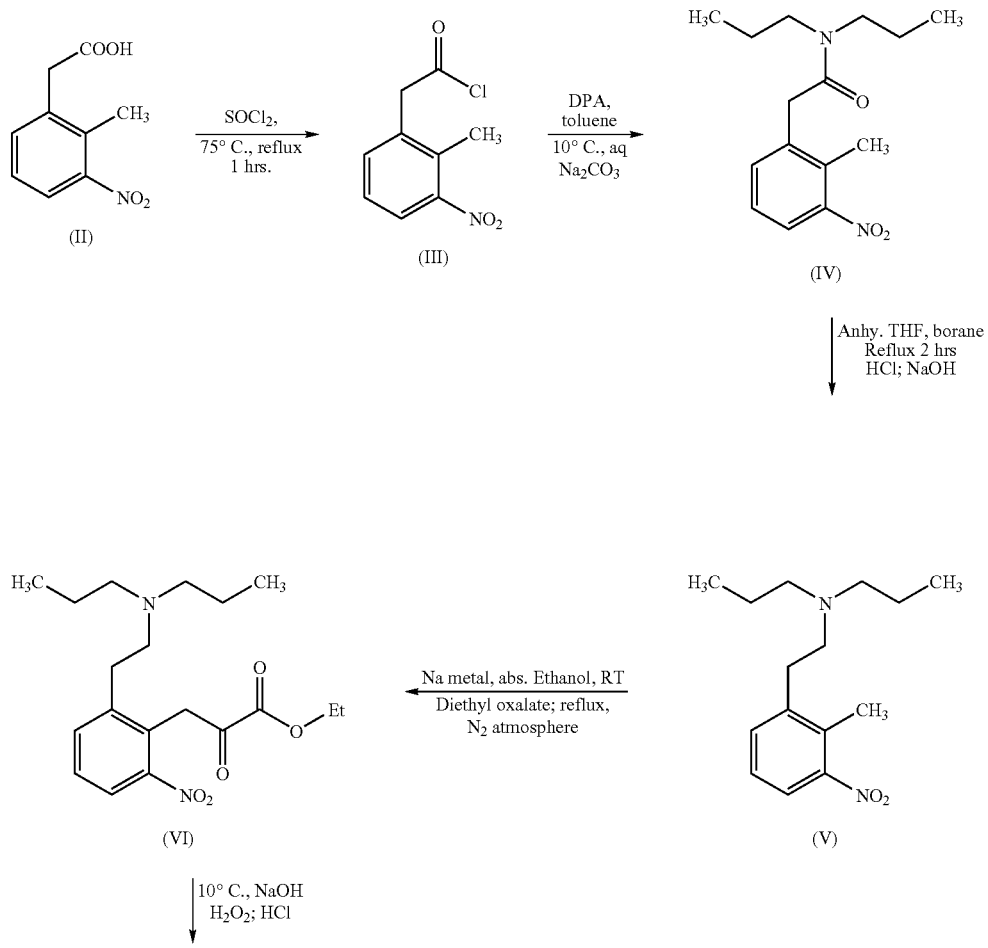

-continued

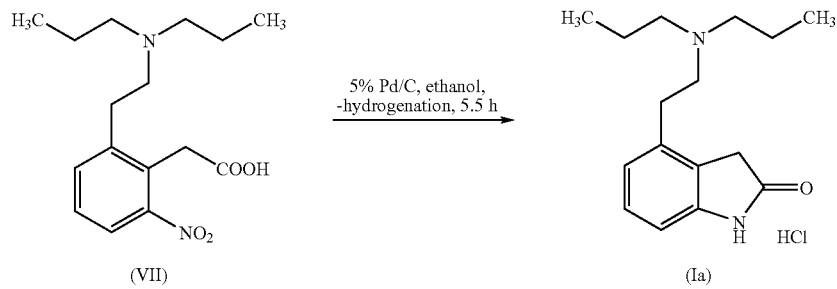

The process as shown above comprises conversion of 2-methyl-3-nitro phenyl acetic acid (II) with thionyl chloride to 2-Methyl-3-nitro-phenylacetyl chloride (III), which upon reaction with Di-n-propyl amine (DPA) gives 2-Methyl-3-nitro phenyl-N,N-di-n-propyl acetamide (IV) in syrup form. This intermediate (IV) is further reduced with Borane/THF and subsequent treatment with HCl/NaOH to give 2-Methyl-3-nitro phenyl ethyl-N,N-di-n-propyl amine (V). Further, compound (V) is treated with Na metal, Ethanol and diethyl oxalate to obtain Ethyl 6-(2-di-n-propylaminoethyl)-2-nitro-phenyl pyruvate (VI), which is further treated with hydrogen peroxide, NaOH and HCl and converted to 6-(2-Di-n-propylaminoethyl)-2-nitro phenyl acetic acid hydrochloride (VII). This intermediate is reduced with palladium/carbon to give Ropinirole hydrochloride (Ia).

Alternative process for the preparation of Ropinirole is described in J. Med. Chem. 1985, 28, 1533-1536 as shown in Scheme-2. The process comprises, the reduction 2-Methyl-3-nitro-benzoic acid (VIII) with diborane to carbinol of formula (IX). The carbinol compound (IX) is chlorinated with thionyl chloride in pyridine to give highly lachrymatory compound of formula (X), which is further converted to compound of formula (XII) by reaction with Potassium cyanide and followed by hydrolysis. 2-methyl-3-nitrophenyl acetic acid (XII) is converted to its acid chloride with thionyl chloride and treated with Di-n-propylamine to give 2-Methyl-3-nitrophenyl-N,N-di-n-propyl acetamide of formula (IV). The compound of formula (IV) is further reduced with borane in THF under reflux to give 2-Methyl-3-nitrophenylethyl-N,N-di-n-propyl amine (V). The amine of formula (V) is reacted with potassium metal in Ethanol and diethyl oxalate resulting in compound (VI) (where R=H), which is treated with hydrogen peroxide, NaOH and HCl to give the intermediate 2-Nitro-6-(2-di-n-propylaminoethyl)-phenyl acetic acid hydrochloride of formula (VII). This intermediate is hydrogenated on palladium/carbon in ethanol to give desired compound Ropinirole hydrochloride of formula (Ia)

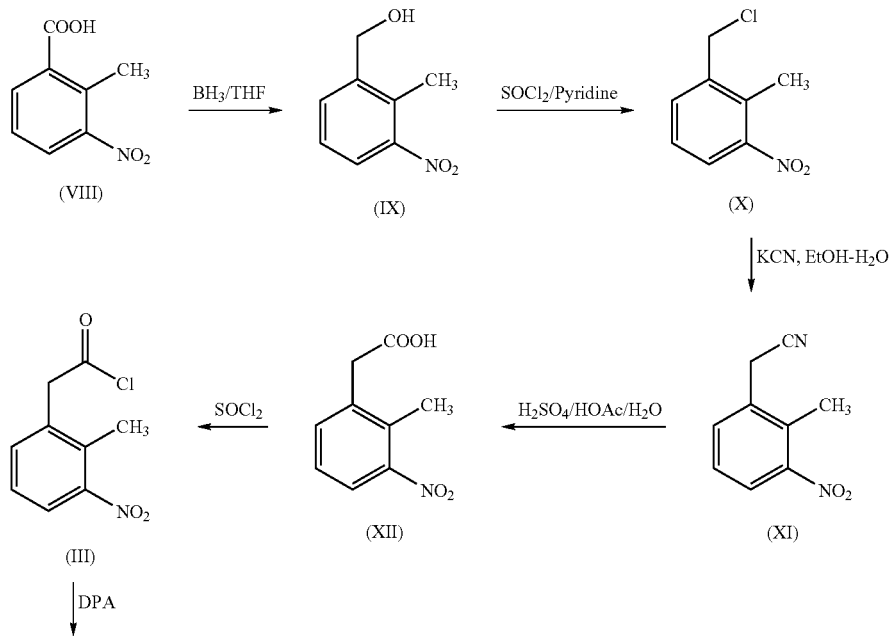

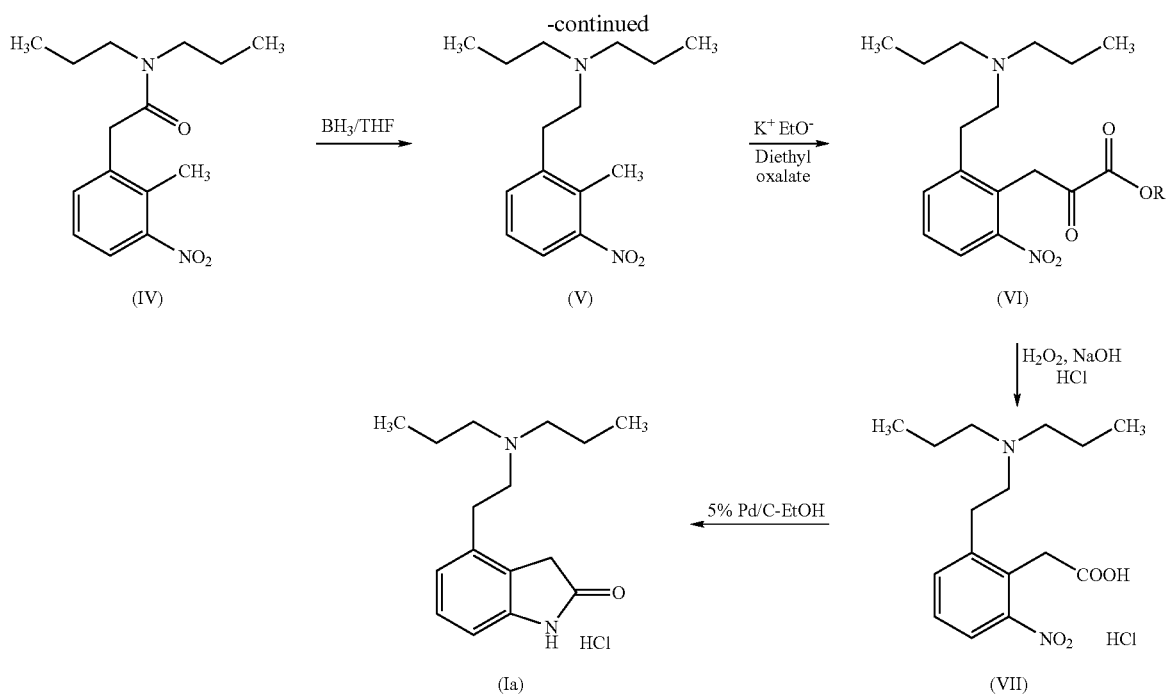

However, the above described process suffers with the following drawbacks:
(i) 2-Methyl-3-nitro benzyl chloride of formula (X) is highly lachrymator and very difficult to handle at commercial production
(ii) The reduction of 2-Methyl-3-nitro benzoic acid (VIII) is carried out with borane/THF, which is highly flammable and hazardous for handling in an industrial scale.
(iii) It involves the use of potassium cyanide in the cynation reaction for the preparation of 2-Methyl-3-nitro benzyl cyanide. Potassium cyanide is highly toxic substance and requires special precaution for its use in production. It is highly desirable to avoid such toxic material.
(iv) Also, this process gives lower yield
(v) Additionally, isolation of intermediate compound of formula (V) as described in Scheme 1 requires the use of Kugelrohr apparatus. Use of such apparatus for commercial production is not feasible.

Overall, the process for the preparation of Ropinirole hydrochloride described in the prior art having disadvantage with respect to the use of toxic, lachrymator material and special apparatus in the process. Also, it gives lower yield. Hence, the process is not feasible for commercial production. So, there is a need for the process for the preparation of Ropinirole hydrochloride, which is easy to handle, suitable for commercial production and obviates the shortcomings of the known processes.

OBJECT OF THE INVENTION

The main object of the invention is to provide a novel process for the preparation of Ropinirole of formula (I) and its pharmaceutically acceptable salts, solvates.

Also, the object of the present invention is to provide a novel process for the preparation of Ropinirole of formula (I) and its pharmaceutically acceptable salts, solvates, which is simple, easy to handle, suitable for commercial production and obviates the shortcomings of the known processes.

Another object of the present invention is to provide novel compounds of formula B, which are useful as an intermediate for the preparation of Ropinirole of formula (I) and its pharmaceutically acceptable salts, solvates.

Yet another object of the present invention is to provide a process for the preparation novel compounds of formula (B).

Still another object of the invention is to provide a novel compound of formula (A), which is useful as an intermediate for the preparation of Ropinirole of formula (I) and its pharmaceutically acceptable salts, solvates.

SUMMARY OF THE INVENTION

According the one embodiment of the present invention, there is provided a process for the preparation of 4-[2-(Di-n-propylamino)ethyl]-2,3-dihydro-1H-indol-2-one of formula (I) and its pharmaceutically acceptable salts, solvates.

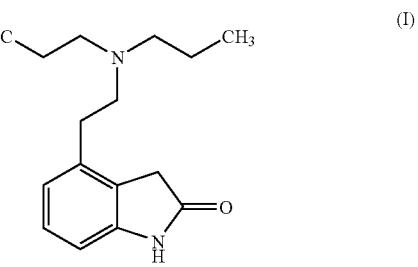

(I)

which comprises
(a) reducing 2-methyl-3-nitro benzoic acid of formula (VIII) with alkali metal borohydride in presence of sulfonic acid or sulfuric acid, to give 2-methyl-3-Nitrobenzyl alcohol of formula (IX)

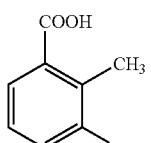

(VIII)

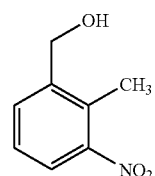

(IX)

(b) converting 2-Methyl-3-nitro benzyl alcohol of formula (IX) to 2-methyl-3-nitrophenyl acetic acid of formula (XII)

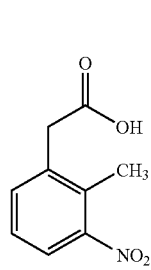

(XII)

(c) reducing 2-Methyl-3-nitrophenyl acetic acid of formula (XII) with alkali metal borohydride in presence of sulfonic acid or sulfuric acid, to give novel 2-Methyl-3-nitro-phenyl ethyl alcohol of formula (A)

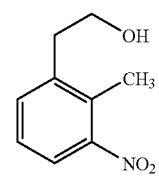

(A)

(d) reacting 2-Methyl-3-nitro phenyl ethyl alcohol of formula (A) with halogenating agent or compounds of formula $R_1$—X, in presence of organic base to give novel compound of formula (B)

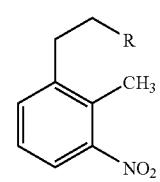

(B)

wherein R represents a halogen atom, lower alkanesulfonyloxy group, substituted or unsubstituted arylsulfonyloxy group, arylkylsulfonyloxy group; $R_1$ represent lower alkanesulfonyloxy, substituted or unsubstituted arylsulfonyloxy, arylalkylsulfonyloxy and X represent a halogen atom.

(e) reacting compound of formula (B) with Di-n-propylamine or its salt, to give 2-Methyl-3-nitrophenylethyl-N,N-di-n-propyl amine of formula (V)

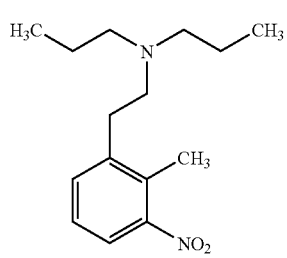

(V)

(f) optionally treating 2-Methyl-3-nitrophenylethyl-N,N-di-n-propyl amine of formula (V) with acid to prepare 2-Methyl-3-nitrophenylethyl-N,N-di-n-propyl amine acid addition salt (g) converting 2-Methyl-3-nitrophenylethyl-N,N-di-n-propyl amine (V) or its acid addition salts to 4-[2-(Dipropylamino)ethyl]-2,3-dihydro-1H-indol-2-one of formula (I) or its pharmaceutically acceptable salts, solvates.

According the another embodiment of the present invention, there is provided a novel compound of formula (A)

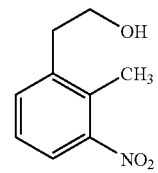

(A)

According to a further embodiment of the present invention, there is provided a novel compound of formula (B)

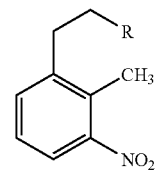

(B)

wherein R represents a halogen atom, or a group causing the same substitution reaction as that caused by halogen atom selected from lower alkanesulfonyloxy group, substituted or unsubstituted arylsulfonyloxy group, arylalkylsulfonyloxy group.

According to another embodiment, there is provided a process for the preparation of novel compounds of formula (A) and if desired the compounds of formula (B), the process comprising (a) reducing 2-Methyl-3-nitro-benzoic acid of formula (VIII) with alkali metal borohydride in presence of sulfonic acid or sulfuric acid, to give 2-Methyl-3-nitro benzyl alcohol of formula (IX)

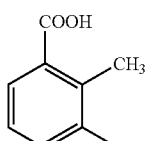
(VIII)

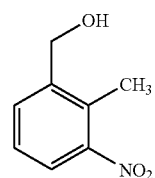
(IX)

(b) converting 2-Methyl-3-nitro benzyl alcohol of formula (IX) to 2-Methyl-3-nitro phenyl acetic acid of formula (XII)

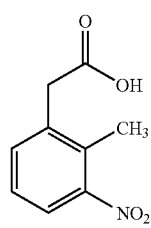
(XII)

(c) reducing 2-Methyl-3-nitrophenyl acetic acid of formula (XII) with alkali metal borohydride in presence of Sulfonic acid or Sulfuric acid, to give novel 2-Methyl-3-nitro phenyl ethyl alcohol of formula (A)

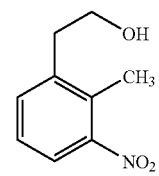
(A)

if desired, reacting 2-Methyl-3-nitro phenyl ethyl alcohol of formula (A) with halogenating agent or compounds of formula $R_1$—X, in presence of organic base to give novel compound of formula (B)

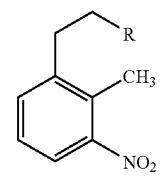
(B)

wherein R represents a halogen atom, lower alkanesulfonyloxy group, substituted or unsubstituted arylsulfonyloxy group, arylalkylsulfonyloxy group; $R_1$ represent lower alkanesulfonyloxy, substituted or unsubstituted arylsulfonyloxy, arylalkylsulfonyloxy and X represent a halogen atom.

DETAILED DESCRIPTION OF THE INVENTION

As stated above the process for the preparation of 4-[2-(Di-n-propylamino)ethyl]-2,3-dihydro-1H-indol-2-one of formula (I) namely Ropinirole and its pharmaceutically acceptable salts, solvates

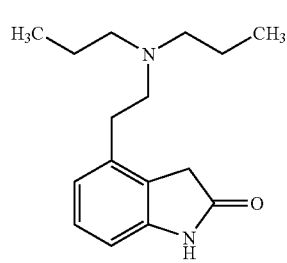
(I)

which comprises
(a) reducing 2-Methyl-3-nitro benzoic acid of formula (VIII) with alkali metal borohydride in presence of sulfonic acid or sulfuric acid, to give 2-Methyl-3-nitro-benzyl alcohol of formula (IX)

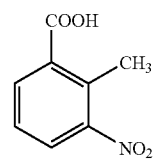
(VIII)

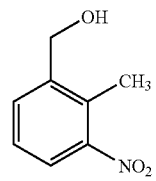
(IX)

(b) converting 2-Methyl-3-nitro benzylalcohol of formula (IX) to 2-Methyl-3-nitrophenylacetic acid of formula (XII)

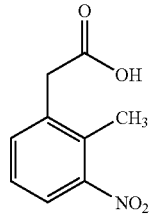
(XII)

(c) reducing 2-Methyl-3-nitro phenyl acetic acid of formula (XII) with alkali metal borohydride in presence of sulfonic acid or sulfuric acid, to give novel 2-Methyl-3-nitro phenyl ethyl alcohol of formula (A)

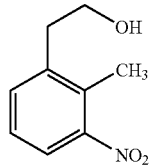

(A)

(d) reacting 2-Methyl-3-nitro phenyl ethyl alcohol of formula (A) with halogenating agent or compounds of formula R₁—X, in presence of organic base to give novel compound of formula (B)

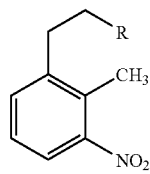

(B)

wherein R represents a halogen atom, lower alkanesulfonyloxy group, substituted or unsubstituted arylsulfonyloxy group, arylalkylsulfonyloxy group; R₁ represent lower alkanesulfonyloxy, substituted or unsubstituted arylsulfonyloxy, arylalkylsulfonyloxy and X represent a halogen atom.

(e) reacting compound of formula (B) with Di-n-propylamine or its salt, to give 2-Methyl-3-nitro phenylethyl-N,N-di-n-propyl amine of formula (V)

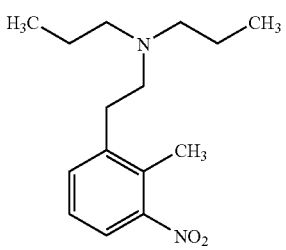

(V)

(f) optionally treating 2-Methyl-3-nitrophenylethyl-N,N-di-n-propylamine of formula (V) with acid to prepare 2-methyl-3-nitrophenylethyl-N,N-di-n-propyl amine acid addition salt (g) converting 2-Methyl-3-nitrophenylethyl-N,N-di-n-propylamine (V) or its acid addition salts to 4-[2-(Di-n-propylamino)ethyl]-2,3-dihydro-1H-indol-2-one of formula (I) or its pharmaceutically salts, solvates.

The alkali metal borohydride used in step (a) is selected from sodium borohydride, potassium borohydride, Lithium borohydride. The preferred alkali metal borohydride is sodium borohydride.

The reaction step (a) is carried out in ethereal solvent. The ethereal solvent is selected from tetrahydrofuran, dioxane, diethyl ether, diisopropyl ether, dimethoxyethane. The preferred ethereal solvent is tetrahydrofuran.

The reaction step (a) is carried out in presence of sulfonic acid or sulfuric acid. The sulfonic acid can be selected from methane sufonic acid, ethane sulfonic acid. The preferred sulfonic acid is methane sulfonic acid.

The conversion of 2-Methyl-3-nitro benzyl alcohol of formula (IX) to 2-methyl-3-nitrophenyl acetic acid (XII) as said in step (b) comprises (i) reacting 2-Methyl-3-nitro benzyl alcohol of formula (IX) with methane sulfonyl chloride in presence of base in halogenated solvent to prepare 2-Methyl-3-nitro benzyl methanesulfonate (XIII)

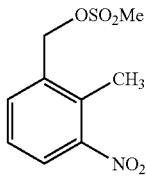

(XIII)

As the base used in step (i) can be selected from organic base preferably Triethyl amine and halogenated solvent can be selected from Methylene dichloride, Ethylene dichloride, Chloroform, Carbon tetrachloride. The preferred halogenated solvent is Methylene dichloride.

(ii) reacting 2-Methyl-3-nitrobenzyl methanesulfonate of formula (XIII) with sodium cyanide in an aqueous acetonitrile to give 2-Methyl-3-nitrophenyl acetonitrile (XI)

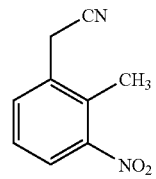

(XI)

The reaction step (ii) is carried out at temperature 60 to 90° C.

(iii) reacting 2-Methyl-3-nitrophenyl acetonitrile (XI) with H₂SO₄ in presence of acetic acid to give 2-Methyl-3-nitro phenylacetic acid (XII)

The 2-Methyl-3-nitro-benzyl alcohol of formula (IX) to 2-Methyl-3-nitro phenylacetic acid (XII) can be carried out without isolating intermediates, which is highly desirable to minimize the labor, time and cost for the production. Also above reaction step (i), (ii) and (iii) can be carried out separately and intermediates (XIII) and (XI) can be isolated.

2-Methyl-3-nitro phenylacetic acid of formula (XII) is reduced with alkali metal borohydride in presence of sulfonic acid or sulfuric acid to give novel 2-(2-Methyl-3-nitrophenyl) ethanol of formula (A) as said in step (c)

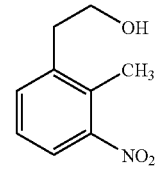

(A)

The alkalimetal borohydride used in the step (c) can be selected from sodium borohydride, potassium borohydride and lithium borohydride. The preferred alkali metal borohydride is sodium borohydride.

The reaction step (c) is carried out in presence of sulfonic acid or sulfuric acid. It is preferably carried out in presence of sulfonic acid.

The sulfonic acid used in step (c) can be selected form methane sulfonic acid or ethane sulfonic acid. The preferred sulfonic acid is methane sulfonic acid.

The reaction step (c) is carried out in ethereal solvent. The ethereal solvent is selected from Tetrahydrofuran, Dioxane, Diethylether, Diisopropyl ether and 1,2-Dimethoxy ethane. The preferred etheral solvent is tetrahydrofuran.

The novel compound of formula (A) is further reacted with halogenating agent or compounds of formula R₁—X, in presence of organic base or to give novel compounds of formula (B)

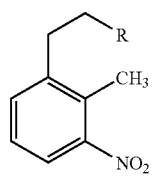

(B)

wherein R represents
- (i') a halogen atom selected from fluorine, chlorine atom, bromine atom and iodine atom; (ii') lower alkanesulfonyloxy group selected from methanesulfonyloxy, ethanesulfonyloxy, isopropanesulfonyloxy, propanesulfonyloxy, butanesulfonyloxy, tert-butanesulfonyloxy, pentanesulfonyloxy, hexanesulfonyloxy;
- (iii') substituted or unsubstituted arylsulfonyloxy group selected from benzene sulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy;
- (iv') arylalkylsulfonyloxy group selected from benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulonyloxy, 4-methoxybenzylsulfonyloxy, 3-chlorobenzylsulfonyloxy Among the above groups represented by R, particularly the preferred group is chloride, bromide, 4-methyphenyl sulfonyloxy, methane sulfonyloxy.

X represent Cl, Br, I and R₁ represents lower alkanesulfonyloxy group, substituted or unsubstituted arylsulfonyloxy group and arylalkylsulfonyloxy group as described above.

Organic base used in step (d) is selected from triethyl amine, N,N-diisopropyl ethylamine, diisopropyl amine, pyridine, piperidine, 1,8-Diazabicyclo[5.4.0]undec-7-ene [DBU]. The preferred organic base is triethyl amine.

The reaction step (d) is carried out in halogenated solvent selected from methylene dichloride, ethylene dichloride, chloroform, carbon tetra chloride. The preferred halogenated solvent is methylene dichloride.

Halogenating agent can be used in step (d) is selected from thionyl chloride, phosphorous pentachloride and other known halogenating agent. Preferably, the halogenating agent can be thionyl chloride.

In preferred way, 2-(2-Methyl-3-nitrophenyl) ethanol of formula (A) is reacted with p-toluenesulfonyl chloride in presence of triethyl amine in halogenated solvent like methylene dichloride to give 2-(2-Methyl-3-nitrophenyl)ethyl-4'-methylbenzene sulfonate, which is further converted to Ropinirole hydrochloride (Ia)

The novel compound of formula (B) is further reacted with Di-n-propyl amine or its salts to give 2-methyl-3-nitrophenylethyl-N,N-di-n-propyl amine of formula (V) as said in step (e). The reaction step (e) is carried out in water at temperature from 30 to 90° C. and more preferably at 70 to 85° C.

Optionally, 2-methyl-3-nitrophenylethyl-N,N-di-n-propyl amine of formula (V) is converted to its acid addition salts by treatment with acid as said in step (f). The acid can be selected from organic acid or inorganic acid. The preferred acid can be selected from hydrochloric acid, sulfuric acid, phosphoric acid, acetic acid, citric acid, maleic acid, malonic acid, oxalic acid, succinic acid, malic acid and tartaric acid. The most preferred acid is oxalic acid.

The compound of formula (V) or its acid addition salts is converted to 4-[2-(Dipropylamino) ethyl]-2,3-dihydro-1H-indol-2-one of formula (I) or its pharmaceutically acid addition salts, solvates according to step (g), which comprises (ia) reacting 2-Methyl-3-nitrophenylethyl-N,N-di-n-propyl amine (V) or its acid addition salt with Diethyl oxalate in presence of alkali metal alkoxide or alkali metal hydride in aprotic solvent selected from dimethyl formamide, dimethyl acetamide, dimethyl sulfoxide, tetrahydrofuran, to give Ethyl-6-(2-di-n-propylaminoethyl)-2-nitrophenylpyruvate of formula (VI). Alkali metal alkoxide can be selected from selected from sodium methoxide, sodium ethoxide, sodium propoxide, potassium methoxide, potassium ethoxide, potassium propoxide or potassium tert-butoxide. Alkali metal hydride can be selected from sodium hydride, potassium hydride. Preferred alkali metal hydride is sodium hydride.

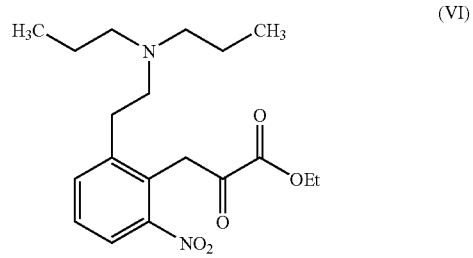

(VI)

Preferably fresh alkali metal alkoxide is used in the reaction. Fresh alkali metal alkoxide is prepared by addition of alkali metal in alcohols. The preferred alkali metal alkoxide is sodium ethoxide, which is prepared by addition of Sodium metal in Ethanol just before the reaction. It is more advantageous to prepare sodium ethoxide in the same reactor of the above process. The reaction is preferably is carried out in Tetrahydrofuran Ethyl-6-(2-di-n-propylaminoethyl)-2-nitrophenylpyruvate of formula (VI) can also prepared by reacting 2-Methyl-3-nitrophenylethyl-N,N-di-n-propyl amine (V) or its acid addition salt with (iia) converting Ethyl-6-(2-di-n-propylaminoethyl)-2-nitrophenylpyruvate of formula (VI) to 2-Nitro-6-(2-di-n-propylaminoethyl)-phenyl acetic acid hydrochloride of formula (VII)

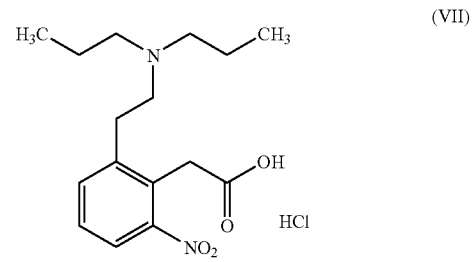

(VII)

(iiia) reducing said compound of formula (VII) with reducing agent to prepare 4-[2-(Di-n-propylamino)ethyl]-2,3-dihydro-1H-indol-2-one of formula (I) or its pharmaceutically acid acceptable salts, solvates.

The above reaction step (ia) to (iiia) can also be carried insitu without isolating intermediate.

2-Nitro-6-(2-di-n-propylaminoethyl)-phenyl acetic acid hydrochloride of formula (VII) is reduced with reducing agent like palladium/carbon to give 4-[2-(Di-n-propylamino)ethyl]-2,3-dihydro-1H-indol-2-one of formula (I) or its pharmaceutically acid acceptable salts, solvates as per the method known per se.

2-Nitro-6-(2-di-n-propylaminoethyl)-phenyl acetic acid hydrochloride of formula (VII) is reduced with 5% palladium/carbon in ethanol to give -[2-(Di-n-propylamino) ethyl]-2,3-dihydro-1H-indol-2-one hydrochloride of formula (Ia).

The process for preparation of compound of formula (A), formula (B) and conversion to Ropinirole hydrochloride is shown in following Reaction Scheme 3:

Thus, the present invention provides an efficient process for the preparation of Ropinirole of formula (I) and its pharmaceutically acceptable salts, solvates, which offers significant commercial advantages when preparing on an industrial scale. The present invention is having several advantages over known process.

The process of the present invention produces Ropinirole of formula (I) and more particularly Ropinirole hydrochloride is simple, environment friendly and economical and leads to an enhanced yield.

The current process further provides significant efficiencies at the commercial manufacturing. The overall cost and labor of the manufacturing process are reduced, as simpler machinery can be used and simple method is involved, all of which provides distinct commercial advantages for the preparation of Ropinirole hydrochloride on a commercial scale.

The process of the present invention is described by the following examples, which are illustrative only and should

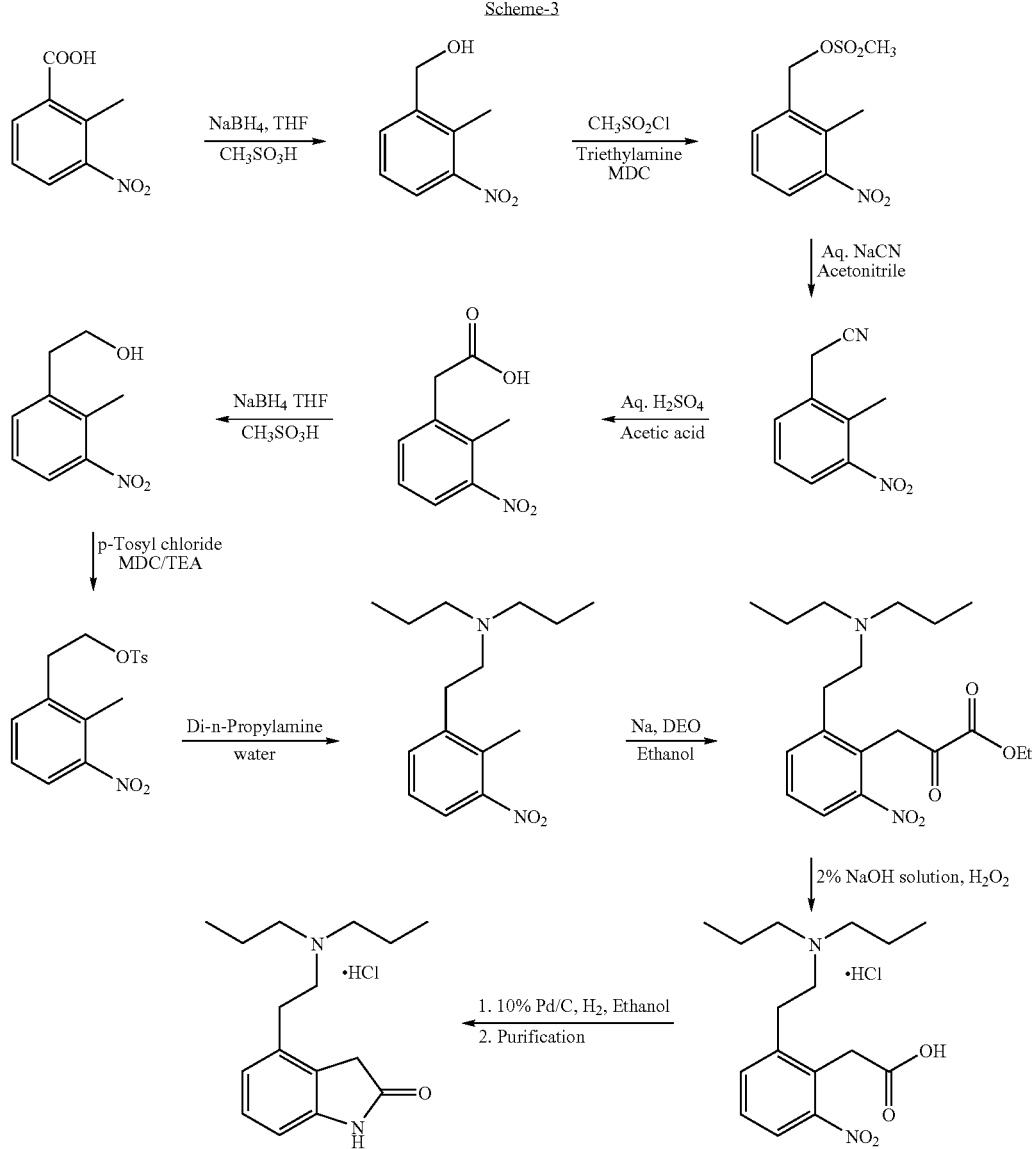

Scheme-3

EXAMPLES

Example 1

Preparation of 2-Methyl-3-nitrobenzyl alcohol 500 ml of THF and 76.5 gm $NaBH_4$ was stirred for 30 min. at ambient temperature. Solution of 2-Methyl-3-nitro benzoic acid in THF (250 g in 750 ml) was added and stirred for 0.5 hour at ambient temperature. Further, methanesulphonic acid (90 ml) was added to the reaction mixture and stirred until the completion of reaction. The reaction mixture is extracted with ethyl acetate by addition of Hydrochloric acid and product organic layer is separated out. Ethyl acetate is evaporated to give 2-Methyl-3-nitrobenzyl alcohol as yellow oil, which is further treated with cyclohexane and crystallized to give 2-Methyl-3-nitrobenzyl alcohol (Yield: ~210 g., 84%)

Example 2

Preparation of 2-Methyl-3-nitrophenylaceticacid

2-Methyl-3-nitro benzyl alcohol (250 g.) is dissolved in Dichloromethane (2500 ml). Triethyl amine (356 ml) is added. Further, methanesulfonylchloride (354 ml) is added to the reaction mixture and stirred until completion of reaction. Dichloromethane is distilled out and Acetonitrile (1000 ml) is added to the reaction mass. Further, solution of Sodium cyanide (79 g) is added to reaction mixture and reaction mixture is refluxed until the completion of reaction. Water (250 ml) and Dichloromethane (1500 ml) are added to the residue after distillation of Acetonitrile. Organic layer is separated and concentrated. Water (920 ml) and Acetic acid (735 ml) is added to the residue at ambient temperature. Further, Sulphuric acid (790 ml) is added to it and refluxed for 7 to 12 h. The reaction mixture is cooled and water is added to crystallize, isolated and dried to give 2-Methyl-3-nitrophenylaceticacid (Yield: ~150 g, ~51%)

Example-3

Preparation of 2-Methyl-3-nitrobenzyl methanesulfonate 200 g 2-Methyl-3-nitro benzylalcohol is added to dichloromethane (2000 ml) and triethylamine (250 ml). Mesyl chloride is added drop wise while maintaining temperature between 0-10° C. and stirred until the completion of reaction. It is further stirred 2 hours at room temperature. Water is added to the reaction mixture and stirred for 10 minutes. Organic layer was separated and washed with brine. Dichloromethane was evaporated to yield the oily brown 2-Methyl-3-nitrobenzyl methanesulfonate (207-210 g).

Example-4

Preparation of 2-Methyl-3-nitro-phenyl acetonitrile

2-Methyl-3-nitrobenzyl methanesulfonate (207 g ) dissolved in Acetonitrile (625 ml). A solution of (41.5 g) sodium cyanide in 200 ml pure water was added to the above solution and refluxed at 80-95° C. until the completion of reaction. Acetonitrile was distilled out and 1000 ml water was added to the residue followed by addition of 1000 ml dichloromethane. The mixture was stirred for 15 minutes followed by extraction. Dichloromethane is distilled out from organic layer and Cyclohexane is to the residue and stirred for 30 minutes to get 2-Methyl-3-nitro-phenylacetonitrile. It is filtered and dried to give 2-Methyl-3-nitro phenylacetonitrile (150-160 g) as brown solid.

Example-5

Preparation of 2-Methyl-3-nitro phenylaceticacid 150 g of 2-Methyl-3-nitro phenylacetonitrile is added to 750 ml pure water and 600 ml acetic acid. 675 ml sulfuric acid is added drop wise to the reaction mixture and refluxed for 6-7 hours. After completion of reaction, 2000 ml water is added to it and stirred for 30-45 minutes, filtered and dried to give 2-Methyl-3-nitro phenylaceticacid (130-135 g).

Example-6

Preparation of 2-Methyl-3-nitro phenylethyl alcohol

A solution of 2-Methyl-3-nitro phenylaceticacid (160 g) in Tetrahydrofuran (480 ml) is added to Sodium borohydride (75 g) and Tetrahydrofuran (160 ml). Further, Methanesulfonicacid (53 ml) is added to reaction mixture at ambient temperature and stirred at 60-75° C. until the completion of reaction. 3N Hydrochloric acid (384 ml) is added to reaction mixture followed by addition of water (1420 ml). Reaction mixture is extracted twice with Dichloro methane (1×800 ml and 1×400 ml) and organic layer is separated. The combined organic layer is washed with $NaHCO_3$ solution and brine solution. Dichloromethane is distilled out under vacuum at 40-50° C. to obtain 2-Methyl-3-nitro phenyl ethyl alcohol as dark brown oil (~145 g).

Example-7

Preparation of 2-Methyl-3-nitro phenylethyl tostylate

2-Methyl-3-nitrophenyl ethyl alcohol (145 g) is dissolved in Dichloromethane (1080 ml). Triethylamine (1125 ml) and p-Toluene sulfonylchloride (216 g) are added to it at 25-30° C. The reaction mixture is stirred for 9-15 h. It is further cooled and 5N Hydrochloric acid (730 ml), Dichloro methane (730 ml) added to it. Organic layer is separated by extraction and washed with water and brine solution. Dichloromethane is distilled off from organic layer under vacuum at 40-45° C. and Methanol (140 ml) is added to residual mass and distilled out the same under vacuum. Cyclohexane (730 ml) is added to the residual mass and stir for 15-30 minutes at ambient temperature, filtered and dried to give 2-Methyl-3-nitro phenylethyl tosylate

Example-8

Preparation of 2-Methyl-3-nitro phenylethyl methanesulfonate

2-Methyl-3-nitrophenyl ethyl alcohol (100 g) is dissolved in (1000 ml) Dichloromethane. Triethylamine (1000 ml) and Methane sulfonyl chloride are added to it at 0 to 10° C. The reaction mixture is stirred for 9-15 h. It is further cooled and mixture of 5N Hydrochloric acid and water is added to it. Organic layer is separated by extraction and washed with water and brine solution. Dichloromethane is distilled off from organic layer under vacuum at 40-45° C. to give oily brown 2-Methyl-3-nitro phenylethyl methanesulfonate.

Example-9

Preparation of 2-Methyl-3-nitro phenylethyl chloride

2-Methyl-3-nitrophenyl ethyl alcohol (100 g) is added to toluene (500 ml). $POCl_3$ (62 ml) is added to the reaction mixture and refluxed for 2 to 3 hrs. Toluene is distilled off completely to give 2-Methyl-3-nitro phenylethyl chloride Example-10

Preparation of 2-Methyl-3-nitro phenylethyl bromide

2-Methyl-3-nitrophenyl ethyl alcohol (100 g) is added to toluene (500 ml). $POBr_3$ (190 g) is added to the reaction mixture and refluxed for 2 to 3 hrs. Toluene is distilled off completely to give 2-Methyl-3-nitro phenylethyl bromide Example-11

Preparation of 2-Methyl-3-nitro-N,N-di-n-propyl phenylethylammonium oxalate

2-Methyl-3-nitro phenylethyl tosylate is added to solution of Di-n-propyl amine (310 ml) and water (5000 ml) at 25-30° C. The reaction mixture is stirred at 60-90° C. for 8-12 h. After completion of reaction, organic layer is separated out and toluene (250 ml) is added and distilled out. Methanol is added to residue and further solution of oxalic acid (80 g.) in methanol (250 ml) is added to it and stirred at 0-10° C. to obtain solid. It is further filtered and dried to give 2-Methyl-3-nitro-N,N-di-n-propyl phenylethylammonium oxalate Example-12

Preparation of 2-Nitro-6-[2-(N,N-di-n-propyl amino)ethyl]phenylacetic acid hydrochloride 2-Methyl-3-nitro-N,N-Di-n-propyl phenyl ethyl ammonium oxalate (100 g) is added to solution of Sodium hydroxide (2000 ml 1.4%) and stir until the clear solution is obtained. Further, ethyl acetate (500 ml) is added and organic layer separated out, washed with brine solution and dried over Sodium sulphate (20 gm). Ethyl acetate is distilled out under vacuum at 50-60° C. to get residue of 2-Methyl-3-nitro-N,N-di-n-propyl phenyl ethyl amine as a free base (70-72 g)

Sodium metal (freshly cut) (9.14 g) is added in Tetrahydrofuran (280 ml) at ambient temp under $N_2$ atmosphere and Ethanol (70 ml) is added to it drop wise and stirred to obtain fresh sodium ethoxide solution. Diethyl oxalate (43 ml) is slowly added to it and stirred for 15 minutes. 2-Methyl-3-nitro-N-N-di-n-propyl phenyl ethyl amine free base (70-72 g) is added to the reaction mixture at 25-30° C. and stirred for 20-24 hrs at ambient temperature under nitrogen atmosphere. After completion of reaction, THF is distilled out and Ethyl acetate (500 ml) is added to reaction mass. Further, 3N HCl (approx. 40 ml) is added to adjust the pH of reaction mass to 7.5-8.0. Organic layer is separated out and dried over sodium sulphate (25 gm). Ethyl acetate is distilled out to obtain Ethyl-6-(2-di-n-propylaminoethyl)-2-nitro phenylpyruvate.

Further, 2% sodium hydroxide solution (1200 ml) is added to Ethyl-6-(2-di-n-propylaminoethyl)-2-nitro phenylpyruvate and stirred for 10-15 minutes. 30% Hydrogen peroxide (40 ml) is slowly added to it at 5-10° and stirred for 45-60 min. Ethyl acetate (210 ml) is added to the reaction mixture and aqueous layer is separated by extraction. Conc. Hydrochloric acid (80-90 ml) is added to the above aqueous layer to adjust pH to 2.5-3.0 to obtain 2-Nitro-6-[2-(N, N-di-n-propyl amino)ethyl]phenyl acetic acid hydrochloride. It is further filtered and dried to give 2-Nitro-6-[2-(N,N-di-n-propyl amino)ethyl]phenyl acetic acid hydrochloride (yield~35-40 g.).

Example 13

Preparation of 2-Nitro-6-[2-(N,N-di-n-propyl amino)ethyl]phenyl acetic acid hydrochloride 2- Methyl-3-nitro-N,N-di-n-propyl phenyl ethyl ammonium oxalate (34 g) is added to solution of Sodium hydroxide (680 ml, 1.4%) and stir until the clear solution is obtained. Further, ethyl acetate (170 ml) is added and organic layer separated out, washed with brine solution and dried over Sodium sulphate (20 gm). Ethyl acetate is distilled out under vacuum at 50-60° C. to get residue of 2-Methyl-3-nitro-N,N-di-n-propyl phenyl ethyl amine as a free base.

Sodium hydride (7.5 g) is added to Tetrahydrofuran (125 ml) at ambient temperature under Nitrogen atmosphere and stirred for 10-30 minutes. Diethyl oxalate (20 ml) is added to reaction mixture and at 25-45° C. and stirred the solution for 15 minutes. 2-Methyl-3-nitro-N, N-Di-n-propyl phenyl ethyl amine free base as generated above is added to reaction mixture and stirred slowly under nitrogen atmosphere at 25-30° C. for 36-72 hours. After completion of reaction THF is distilled out from the reaction mixture under vacuum at 35-70° C. and Ethyl acetate (250 ml) is added to reaction mass. Further, 3N HCl (approx. 30 ml) is added to adjust the pH of reaction mass to 7.5-8.0. Organic layer is separated out and dried over sodium sulphate. Ethyl acetate is distilled out to obtain Ethyl-6-(2-di-n-propylaminoethyl)-2-nitrophenylpyruvate.

Further, 2% sodium hydroxide solution (500 ml) is added to ethyl-6-(2-di-n-propylaminoethyl)-2-nitrophenylpyruvate and stirred for 10-15 minutes. 30% Hydrogen peroxide (12 ml) is slowly added to it at 5-10° and stirred for 45-60 min. Ethyl acetate (125 ml) is added to the reaction mixture and aqueous layer is separated by extraction. Conc. Hydrochloric acid is added to the above aqueous layer to adjust pH to 2.5-3.0 to obtain 2-Nitro-6-[2-(N,N-Di-n-propyl amino)ethyl]phenyl acetic acid hydrochloride. It is further filtered and dried and recrystallized from acetonitrile to give 2-Nitro-6-[2-(N,N-di-n-propyl amino)ethyl]phenyl acetic acid hydrochloride (yield~10-13 g.).

Example-14

Preparation of Ropinirole hydrochloride

2-Nitro-6-[2-(N,N-Di-n-propyl amino)ethyl]phenyl acetic acid hydrochloride (100 g) is dissolved methanol (2000 ml) and then hydrogenated in presence of 10% Palladium on charcoal. The reaction mixture is filtered to obtain clear solution. Methanol is distilled out under vacuum at 50° C. Isopropanol (100 ml) is added to the residue and it is cooled, filtered and washed with isopropanol to obtain light yellow crystalline Ropinirole hydrochloride. The product is dried at 60-70° C. under vacuum. Yield 65-75 g.

While the present invention has been described in terms of its specific embodiments, certain modifications and equivalents will be apparent to those skilled in the art and are intended to be included within the scope of the present invention.

The invention claimed is:

1. A process for the preparation of 4-[2-(Di-n-propylamino)ethyl]-2,3-dihydro-1H-indol-2-one of formula (I) and its pharmaceutically acceptable salts or solvates

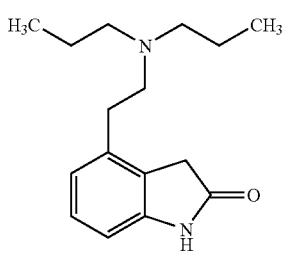

(I)

Comprising:
(a) reducing 2-Methyl-3-nitro-benzoic acid of formula (VIII) with alkali metal borohydride in presence of sulfonic acid or sulfuric acid, to give 2-Methyl-3-nitrobenzyl alcohol of formula (IX);

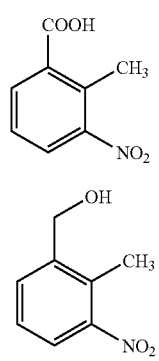

(VIII)

(IX)

(b) converting 2-Methyl-3-nitrobenzyl alcohol of formula (IX) to 2-Methyl-3-nitrophenyl acetic acid of formula (XII);

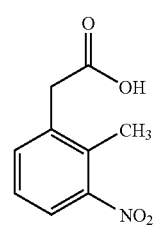

(XII)

(c) reducing 2-Methyl-3-nitrophenyl acetic acid of formula (XII) with alkali metal borohydride in presence of sulfonic acid or sulfuric acid, to give novel 2-Methyl-3-nitro-phenyl ethyl alcohol of formula (A);

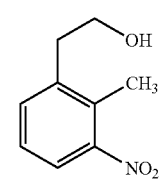

(A)

(d) reacting 2-Methyl-3-nitro-phenyl ethyl alcohol of formula (A) with halogenating agent or compounds of formula $R_1$—X, in presence of organic base to give novel compound of formula (B);

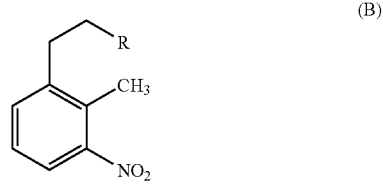

(B)

wherein R represents a halogen atom, lower alkanesulfonyloxy group, substituted or unsubstituted arylsulfonyloxy group, arylalkylsulfonyloxy; $R_1$ represent lower alkanesulfonyloxy, substituted or unsubstituted arylsulfonyloxy, arylalkylsulfonyloxy and X represent a halogen atom;

(e) reacting compound of formula (B) with Di-n-propylamine or its salt, to give 2-Methyl-3-nitrophenylethyl-N,N-di-n-propyl amine of formula (V)

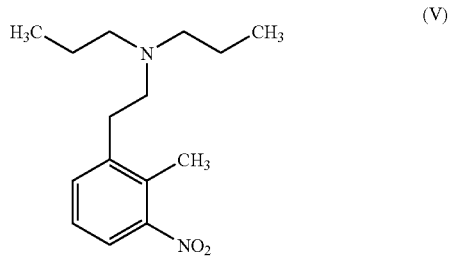

(V)

(f) optionally treating 2-Methyl-3-nitrophenylethyl-N,N-di-n-propyl amine of formula (V) with acid to prepare 2-Methyl-3-nitrophenylethyl-N,N-di-n-propyl amine acid addition salt;

(g) converting 2-Methyl-3-nitrophenylethyl-N,N-di-n-propyl amine (V) or its acid addition salts to 4-[2-(Di-n-propylamino)ethyl]-2,3-dihydro-1H-indol-2-one of formula (I) or its pharmaceutically salts or solvates.

2. A process as claimed in claim 1, wherein the lower alkanesulfonyloxy group is methanesulfonyloxy, ethanesulfonyloxy, isopropanesulfonyloxy, propanesulfonyloxy, butanesulfonyloxy, tert-butanesulfonyloxy, pentanesulfonyloxy, or hexanesulfonyloxy.

3. A process as claimed in claim 1, wherein the substituted or unsubstituted arylsulfonyloxy group is phenylsulfonyloxy, 4-methylphenylsulfonyloxy, 2-methylphenylsulfonyloxy, 4-nitrophenylsulfonyloxy, 4-methoxyphenylsulfonyloxy, or 3-chlorophenylsulfonyloxy.

4. A process as claimed in claim 3, wherein R is 4-methyphenyl sulfonyloxy and $R_1$—X is 4-methylphenyl sulfonyloxy chloride.

5. A process as claimed in claim 1, wherein the arylalkylsulfonyloxy group is benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulonyloxy, 4-methoxybenzylsulfonyloxy, or 3-chlorobenzylsulfonyloxy.

6. A process as claimed in claim 1, wherein X represents Cl, Br, I and $R_1$ represents lower alkanesulfonyloxy, substituted or unsubstituted arylsulfonyloxy and arylalkylsulfonyloxy group.

7. A process as claimed in claim 1, wherein alkali metal borohydride used in step (a) is sodium borohydride, potassium borohydride, or Lithium borohydride.

8. A process as claimed in claim 1, wherein sulfonic acid used in step (a) is methane sufonic acid or ethane sulfonic acid.

9. A process as claimed in claim 1, wherein step (a) is carried out in ethereal solvent selected from tetrahydrofuran, dioxane, diethyl ether, diisopropyl ether, or dimethoxy ether.

10. A process as claimed in claim 1, wherein alkali metal borohydride used in step (a) is about 1.5 to 3 equivalents, relative to the amount of 2-Methyl-3-nitro benzoic acid.

11. A process as claimed in claim 1, wherein conversion of 2-Methyl-3-nitro benzyl alcohol of formula (IX) to 2-Methyl-3-nitrophenyl acetic acid (XII) in step (b) comprises:

(i) reacting 2-Methyl-3-Nitro benzyl alcohol of formula (IX) with Methane sulfonyl chloride in presence of base in halogenated solvent selected from methylene dichloride, ethylene dichloride, chloroform, carbon tetrachloride to prepare 2-Methyl-3-nitrobenzyl methanesulfonate (XIII);

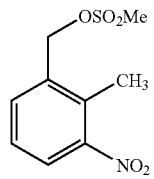

(XIII)

(ii) reacting 2-Methyl-3-nitrobenzyl methanesulfonate of formula (IV) with sodium cyanide in an aqueous acetonitrile at 60 to 90° C. to give 2-(Methyl-3- nitrophenyl) acetonitrile (XI);

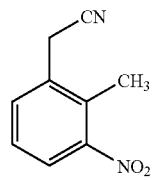

(XI)

(iii) reacting 2-(2-Methyl-3-nitrophenyl)acetonitrile (XI) with $H_2SO_4$ in presence of acetic acid to give 2-(2-methyl-3-nitrophenyl)acetic acid (XII).

12. A process as claimed in claim 11, wherein steps (i), (ii) and (iii) are carried out without isolation of reaction intermediates.

13. A process as claimed in claim 1, wherein alkali metal borohydride used in step (c) is sodium borohydride, potassium borohydride, or Lithium borohydride.

14. A process as claimed in claim 1, wherein sulfonic acid used in step (c) is methane sufonic acid or ethane sulfonic acid.

15. A process as claimed in claim 1, wherein step (c) is carried out in ethereal solvent selected from tetrahydrofuran, dioxane, diethyl ether, diisopropyl ether, or dimethoxy ether.

16. A process as claimed in claim 1, wherein organic base used in step (d) is triethyl amine, diisopropy (ethyl)amine, diisopropyl amine, pyridine, piperadine, or 1,8-Diazabicyclo [5.4.0]undec-7-ene (DBU).

17. A process as claimed in claim 1, wherein organic base used in step (d) has mol. Ratio of 1 to 10:1 of compound of formula (B).

18. A process as claimed in claim 1, wherein said step (d) is carried out in halogenated solvent selected from methylene dichloride, ethylene dichloride, chloroform, or carbon tetrachloride.

19. A process as claimed in claim 1, wherein halogenating agent in said step (d) is thionyl chloride or phosphorus pentachloride.

20. A process as claimed in claim 1, wherein said acid in step (f) is organic acid or inorganic acid.

21. A process as claimed in claim 20, wherein said acid is hydrochloric acid, sulfuric acid, phosphoric acid, acetic acid, citric acid, maleic acid, malonic acid, oxalic acid, succinic acid, malic acid, or tartaric acid.

22. A process as claimed in claim 1, wherein said step (g) comprises:

(ia) reacting 2-Methyl-3-nitrophenylethyl-N,N-di-n-propyl amine (IX) or its acid addition salt with Diethyl oxalate in presence of alkali metal alkoxide or alkali-metal hydride; in aprotic solvent selected from dimethyl formamide, dimethyl acetamide, dimethyl sulfoxide, or tetrahydrofuran, to give Ethyl 6-(2-di-n-propylaminoethyl)-2-nitrophenyl pyruvate (VI);

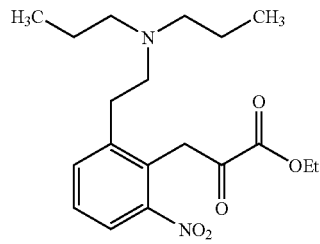

(VI)

(iia) converting Ethyl 6-(2-Di-n-propylaminoethyl)-2-nitrophenyl pyruvate of formula (VI) to 2-Nitro-6(2-di-n-propylaminoethyl)-phenyl acetic acid hydrochloride of formula (VII);

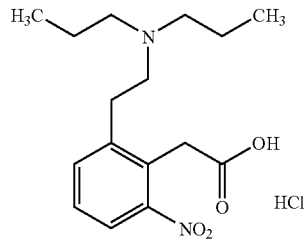

(VII)

(iiia) reducing 2-Nitro-6-(2-di-n-propylaminoethyl)-phenyl acetic acid hydrochloride of formula (VII) with reducing agent to prepare 4-[2-(Di-n-propylamino) ethyl]-2,3-dihydro-1H-indol-2-one of formula (I) or its pharmaceutically acid acceptable salts or solvates.

23. The compound of formula (B)

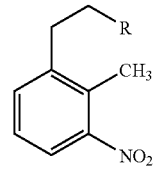

(B)

wherein R represents
  (i) a halogen atom selected from fluorine, chlorine atom, bromine atom, or iodine atom; (ii) lower alkanesulfonyloxy group selected from methanesulfonyloxy, ethanesulfonyloxy, isopropanesulfonyloxy, propanesulfonyloxy, butanesulfonyloxy, tert-butanesulfonyloxy, pentanesulfonyloxy, or hexanesulfonyloxy;
  (iii) substituted or unsubstituted arylsulfonyloxy group selected from phenylsulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy;
  (iv) arylalkylsulfonyloxy group selected from benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulonyloxy, 4-methoxybenzylsulfonyloxy, or 3- chlorobenzylsulfonyloxy.

24. The compound of formula (B) as claimed in claim 23 which is 2-Methyl-3-nitrophenethyl tosylate.

25. The process of claim 11, wherein the base is triethyl amine.

* * * * *